United States Patent
Mizutani et al.

(10) Patent No.: US 7,387,621 B2
(45) Date of Patent: Jun. 17, 2008

(54) INTERLABIAL PAD

(75) Inventors: Satoshi Mizutani, Kagawa (JP); Wataru Yoshimasa, Kagawa (JP); Yuki Noda, Kagawa (JP)

(73) Assignee: Uni-Charm Corporation, Shikokuchuo-Shi, Ehime-Ken (JP)

( * ) Notice: Subject to any disclaimer, the term of this patent is extended or adjusted under 35 U.S.C. 154(b) by 0 days.

(21) Appl. No.: 11/007,577

(22) Filed: Dec. 8, 2004

(65) Prior Publication Data

US 2005/0137558 A1   Jun. 23, 2005

(30) Foreign Application Priority Data

Dec. 9, 2003   (JP) .............................. 2003-411091

(51) Int. Cl.
    *A61F 13/15*    (2006.01)
(52) U.S. Cl. .................... 604/385.17; 604/385.18; 604/385.101; 604/385.21; 604/378
(58) Field of Classification Search ........... 604/385.17, 604/385.18, 385.201, 385.21, 397, 386, 400, 604/402, 385.101, 378
    See application file for complete search history.

(56) References Cited

U.S. PATENT DOCUMENTS

| | | | |
|---|---|---|---|
| 5,336,208 A * | 8/1994 | Rosenbluth et al. | ........ 604/329 |
| 5,672,165 A * | 9/1997 | Belecky et al. | ............. 604/383 |
| 6,183,456 B1 * | 2/2001 | Brown et al. | .......... 604/385.01 |
| 6,183,587 B1 * | 2/2001 | McFall et al. | ............... 156/201 |

FOREIGN PATENT DOCUMENTS

| | | |
|---|---|---|
| JP | 11-500341 A | 1/1999 |
| JP | 2001-474 A | 1/2001 |
| JP | 2002-534162 A | 10/2002 |
| WO | WO-02/094158 A1 | 11/2002 |
| WO | WO-02/094159 A1 | 11/2002 |

OTHER PUBLICATIONS

Abstract of WO 00/40190 (JP 2002-534162) published on Jul. 13, 2000.
Patent Abstracts of Japan for 2001-000474 published on Jan. 9, 2001.
Abstract of WO 97/18784 (JP 11-500341) published on May 29, 1997.

* cited by examiner

*Primary Examiner*—Jacqueline F. Stephens
(74) *Attorney, Agent, or Firm*—Darby & Darby P.C.

(57) ABSTRACT

An interlabial pad with reduced leakage of body fluids is provided by enabling direct absorption and retaining of body fluids at a predetermined site. Disclosed is an interlabial pad having a body fluid absorption capacity. The interlabial pad includes a body fluid outlet contacting region to contact a ostium vaginae and/or urethral meatus in the state of application. At least the body fluid outlet contacting region has a highly absorbing and retaining region having an elevated body fluid absorption capacity to immediately absorb the discharged body fluids, and an elevated body fluid retaining capacity to retain the absorbed body fluids.

7 Claims, 6 Drawing Sheets

INTERLABIAL PAD

CROSS-REFERENCE TO RELATED APPLICATIONS

This application is based upon and claims the benefit of priority from Japanese Patent application No. 2003-411091 filed on Dec. 9, 2003, the entire contents of which is incorporated herein by reference.

1. Field of the Invention

The present invention relates to an interlabial pad applied between female labia. More particularly, the invention relates to an interlabial pad constituted to provide a comfortable wearing feel and a marked effect to prevent body fluid leakage.

2. Related Art

Conventionally, interlabial pads used by insertion between female labia have been known as sanitary items for female use (see, JP-T-11-500341, the term "JP-T" as used herein means a published Japanese translation of a PCT patent application). Because this interlabial pad is applied by insertion of a part thereof between female labia, closer contact with the body can be achieved in comparison with sanitary napkins, leading to less leakage of menstrual blood and the like. Furthermore, they are advantageous in less psychological resistance upon application, compared to tampons that are inserted into vagina. On one hand, although interlabial pads directly absorb body fluids discharged from the wearer's ostium vaginae in the state of application, they have smaller size than sanitary napkins. Therefore, significant problems have been raised in that leakage of body fluids must be prevented without changing the size. Thus, interlabial pads which hardly cause the leakage of body fluids have been investigated (see, JP-T-2002-534162).

An interlabial pad described in JP-T-11-500341 has a substantially elliptic shape having a protruded portion arranged around the central region in the longitudinal direction on a reverse surface of the labia -contacting surface of the covering material. This enables the wearer to bring it into close contact within labia by holding the protruded portion. Moreover, in the interlabial pad described in JP-T-2002-534162, an absorbent layer for storing body fluids is further disposed along the side area in the longitudinal direction on the absorbent body. By means of this body fluid storage layer, leakage of the body fluids from the gap between labia and the interlabial pad can be prohibited.

SUMMARY OF THE INVENTION

However, the interlabial pads described in JP-T-11-500341 and JP-T-2002-534162 both were proposed without taking into account of the state of discharging body fluids, therefore, they involve risks of leakage of the body fluids.

The present invention was made in view of the foregoing problems, and an object thereof is to provide an interlabial pad that exerts an excellent effect to prevent leakage and that is suited for the state of discharge of body fluids.

In order to accomplish the object as described above, the present invention is characterized by avoiding extensive exudation of the body fluids by improving a body fluid absorption capacity and a body fluid retaining capacity in a portion of the interlabial pad which contacts the site where body fluids are discharged.

Specifically, the invention presents the following matters.

(1) An interlabial pad having a body fluid absorption capacity, the interlabial pad being applied by inserting a part or whole thereof between labia, and comprising a body fluid outlet contacting region to contact a ostium vaginae and/or an urethral meatus in the state of application, and wherein at least the body fluid outlet contacting region has a highly absorbing and retaining region having an elevated body fluid absorption capacity to immediately absorb discharged body fluids, and an elevated body fluid retaining capacity to retain the absorbed body fluids.

According to the invention of the item (1), direct and rapid absorption of successively discharged body fluids is enabled by arranging a highly absorbing and retaining region having a high body fluid absorption capacity and a high body fluid retaining capacity at or around a site where the body fluids are discharged. Accordingly, a situation can be prevented in which the body fluids flow between wearer's pudendal slit and on the surface of the interlabial pad, resulting from the saturated state (overflow) through absorption of the body fluids as is caused in conventional interlabial pads. In addition, unlike sanitary napkins, when body fluids (menstrual blood) are entirely spread on a conventional interlabial pad, the body fluids are attached to hands upon taking off the interlabial pad, thus leading to unsanitary affairs. In this respect, the interlabial pad according to the invention is liable to be brought into contact with ostium vaginae and therearound, therefore, the discharged body fluids can be immediately absorbed in a concentrated manner and retained in the interlabila pad. Consequently, the situation as described above can be avoided.

The "body fluid outlet contacting region" is the region that contacts a ostium vaginae and/or an urethral meatus and a peripheral part thereof, and includes any of one or both of ostium vaginae or urethral meatus, or at least either one of ostium vaginae or urethral meatus and a peripheral part thereof. For example, when the highly absorbing and retaining region is arranged at the ostium vaginae and peripheral region thereof, the pad can be used for absorbing menstrual bloods or vaginal discharges.

Interlabial pads having any shape may be involved in the present invention as long as they have a highly absorbing and retaining region in a region where the body fluids are discharged.

(2) The interlabial pad according to the item (1) wherein the interlabial pad has absorbent bodies for absorbing and retaining body fluids, and the highly absorbing and retaining region is formed by laminating the absorbent bodies.

According to the invention of the item (2), by forming the highly absorbing and retaining region through laminating two or more absorbent bodys, a basis weight per unit area (referred to as METSUKE in Japanese) and density of the absorbent body are increased, thereby capable of further elevating the absorption capacity and retaining capacity of the body fluids. Moreover, by laminating a plurality of absorbent bodys, thickness of only the highly absorbing and retaining region can be increased, therefore, abutting on the wearer's ostium vaginae or urethral meatus at a point is permitted in the state of application.

(3) The interlabial pad according to the item (1) wherein the interlabial pad comprises a first sheet element and a second sheet element each having a body fluid absorption capacity; wherein the first sheet element has a front face sheet that contacts a body in the state of application and a back face sheet that is the reverse face of the front face, and has a substantially vertically long shape having a longitudinal direction and a lateral direction; and wherein the highly absorbing and retaining region comprising the second sheet element on the front face sheet or the back face sheet.

According to the invention, sheet elements are double layered in the highly absorbing and retaining region, therefore, wettability and Klemm's water absorbency of the highly absorbing and retaining region become higher in comparison with other region. Additionally, for example, when the second sheet element is disposed above the first sheet element in the highly absorbing and retaining region, a part of the second sheet element may be fixed on the first sheet element. In this instance, the second sheet element preferably has a liquid permeability to permeabilize the absorbed body fluids to the first sheet element. It is preferred that the first sheet element has a body fluid absorption capacity allowing for absorbing the body fluids, and further, that the back face sheet of the first sheet has a liquid impermeability in order to avoid substantial leakage of the absorbed body fluids downwards. Moreover, the interlabial pad may also be configured to permit application through inserting the wearer's finger between the second sheet element and the first sheet element.

Also in cases where the second sheet element is disposed beneath the first sheet element, at least a part of the second sheet element may be fixed on the first sheet element. In this instance, the portion of the first sheet element where the second sheet element is positioned preferably has a liquid permeability to permeabilize the absorbed body fluids to the second sheet element. It is preferred that at a portion of the first sheet element where the second sheet element is not positioned, the back face sheet of such a portion has a liquid impermeability in order to avoid substantial leakage of the absorbed body fluids downwards.

It is preferred that the second sheet element has a body fluid absorption capacity to be able to absorb body fluids permeabilized from the first sheet element or body fluids permeabilized from other part else. Furthermore, in order to avoid substantial leakage of the absorbed body fluids downwards, it is preferred that the back face sheet has a liquid impermeability. Moreover, the interlabial pad may also be configured to permit application through inserting the wearer's finger between the second sheet element and the first sheet element.

(4) A process for adjusting an interlabial pad having a body fluid absorption capacity, the interlabial pad being applied by inserting a part or whole thereof between labia, wherein the process comprising setting a highly absorbing and retaining region having a high body fluid absorption capacity and body fluid retaining capacity in the state of application, and adjusting the position and absorption capacity of the highly absorbing and retaining region. to use the interlabial pad for absorbing vaginal discharges or urine in incontinence.

According to the invention of the item (4), the interlabial pad can be made for use in absorbing vaginal discharges that are discharged from the ostium vaginae other than menstrual blood, or for use in urinary incontinence in order to absorb urine discharged from the urethral meatus, by adjusting the position and absorption capacity of the highly absorbing and retaining region.

As explained hereinabove, the present invention enables to absorb and retain body fluids by elevating the body fluid absorption capacity and the body fluid retaining capacity at a portion of the interlabial pad that abuts on the site where the body fluids outflow. Accordingly, flow of body fluids between wearer's pudendal slit and on the surface of the interlabial pad can be reduced, and thus, a situation of occurrence of leakage of the body fluids, and getting the hand dirty upon removal can be obviated.

DESCRIPTION OF THE PREFERRED EMBODIMENT

Figure 1:
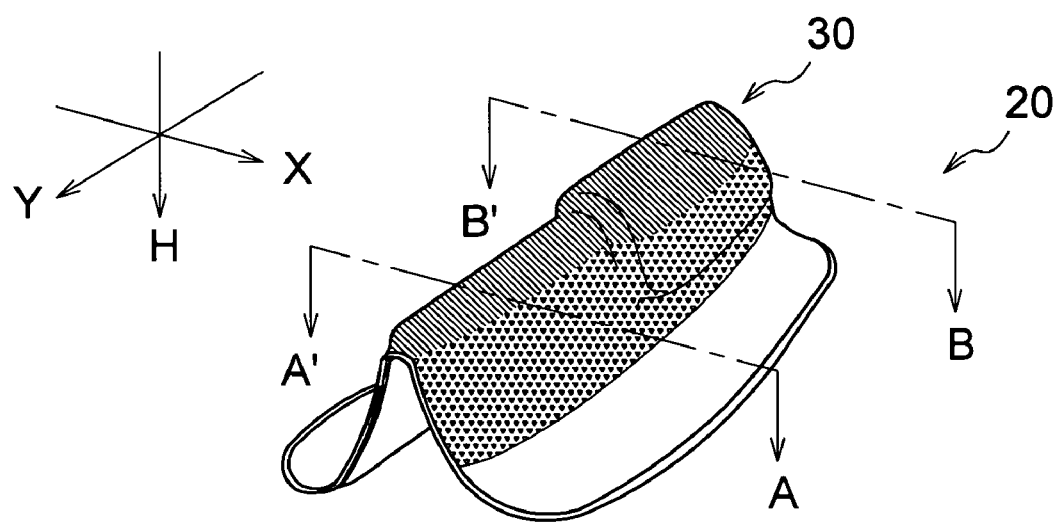
FIG. 1 is a front perspective view illustrating an interlabial pad according to a first embodiment of the present invention.

Hereinafter, the present invention is explained in more detail. In the following description of the embodiments, the identical reference numeral is assigned for the identical constituent element to omit or simplify the explanation thereof.

The interlabial pads according to the embodiments are produced with reference to mean values of females 20's to 50's in age. Specifically, BMI value (=body weight kg/(height m)$^2$) is 21; intracrotch interval in an erect posture is 35 cm; the length of anterior commissure of labia is 60 mm; the length of clitoris is 38 mm; the length of ostium vaginae is 34 mm; and the length of anus is 50 mm. These values were determined by drawing a horizontal line at each part (anterior labial commissure, clitoris, etc.,) in the longitudinal direction of the body and measuring the total distance between the deepest points of the groin that intersect with the horizontal line.

First Embodiment

Overall Structure

First, fundamental overall structure of the interlabial pad of the present invention is explained.

The interlabial pad (hereinafter, referred to as "pad") 20 according to this embodiment has a vertically long shape as shown in FIG. 1, and a substantially gourd shape (constricted in the middle) with the Y-axis being the major axis and the X-axis being the minor axis is exhibited when it is looked down from just above. A highly absorbing and retaining region 30 is disposed on a part of the pad 20. Shape of the pad 20 is not particularly limited as long as the pad can be adapted to female labia, and shapes such as elliptic, gourd shaped, drop shaped, or the like can be chosen. Furthermore, the pad 20 according to this embodiment is of a type for use through folding in two along the longitudinal center line as a fold axis, but not limited thereto. Entire dimension of the outline of the pad 20 in the longitudinal direction is preferably 50 to 180 mm, and more preferably 80 to 120 mm. Moreover, in the lateral direction, it is preferably 30 to 100 mm, and more preferably 50 to 80 mm.

Figure 2:
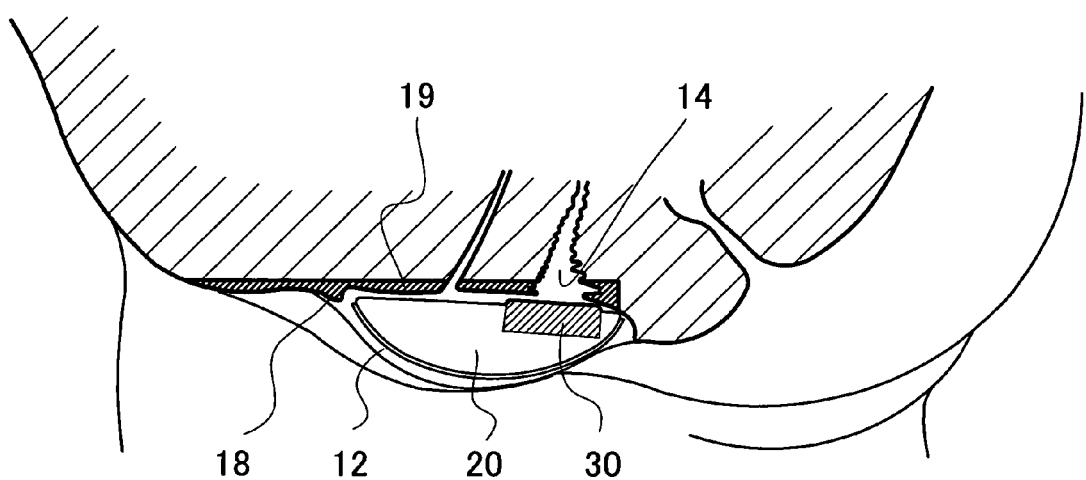
FIG. 2 is a cross sectional view illustrating the state of application of the interlabial pad according to the first embodiment of the invention.

FIG. 2 is a cross sectional view illustrating the state of application of the pad 20. The pad 20 is intervened between the wearer's labia 12, and the highly absorbing and retaining region 30 of the pad 20 contacts the ostium vaginae 14. Therefore, menstrual blood discharged from the ostium vaginae 14 can be absorbed in a concentrated manner. Dimension in the longitudinal direction of this highly absorbing and retaining region 30 is not particularly limited, but preferably, it is not disposed at an anterior part of the vestibular bed 19 including clitoris 18 which is sensitive to stimuli.

Figure 3:
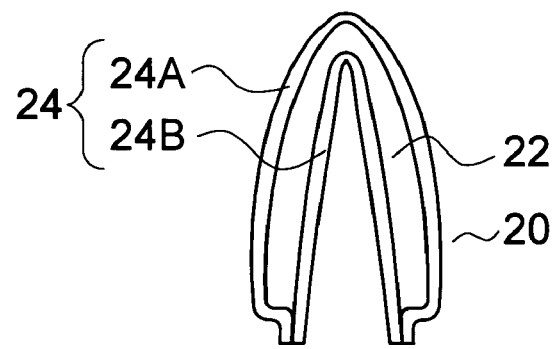
FIG. 3 is a cross sectional view illustrating the interlabial pad according to the first embodiment of the invention.

FIG. 3 is a cross sectional view illustrating the A-A' cross section of the pad 20 shown in FIG. 1. The pad 20 includes an absorbent body 23nd a sheet element 24 covering this absorbent body 22. Each member is fixed with glue or a seal. The portion of the sheet element 24 that contacts the wearer's labia (hereinafter, referred to as front face sheet 24A) is preferably liquid permeable, which allows the body fluids to be permeabilized, while the portion that does not contact the wearer's labia (hereinafter, referred to as back face sheet 24B) is preferably liquid impermeable, which does not allow the body fluids to be permeabilized.

As a liquid impermeable material, a breathable film obtained by drawing a composite sheet of a resin and an inorganic filler, a breathable liquid blocking sheet which has 10 to 30% pores with a pore size falling within the range of from 0.1 to 0.6 mm and which is obtained by arranging capillaries such that they are directed to the absorbent body 22, or the like is preferably used. Examples thereof include polyethylene, polypropylene, polyethylene terephthalate, polyvinyl alcohol, polylactic acids, polybutyl succinate, or nonwoven fabrics, paper, and laminated materials thereof, having a thickness of 15 to 60 μm. Specifically, films prepared using a low density polyethylene (LDPE) resin as a main component to have 10 to 30%. pores, which is adjusted to give the range of the pore size of from 0.1 to 0.6 mm and a basis weight per unit area of 15 to 35 $g/m^2$ may be included. Examples of the nonwoven fabric include spun bond nonwoven fabrics, point bond nonwoven fabrics, through air nonwoven fabrics and the like, which may be subjected to a treatment to provide water repellency. Among them, nonwoven fabrics having a three-layered structure of spun bond/melt blown /spun bond (SMS) including melt blown constituted from extra fine fibers with extremely small intrafiber distances are preferred. In this instance, it is preferably constituted that each of the layers has the basis weight per unit area falling within the range of from 5 to 15 $g/m^2$, from 1 to 10 $g/m^2$, and from 5 to 10 $g/m^2$, respectively.

Figure 4:
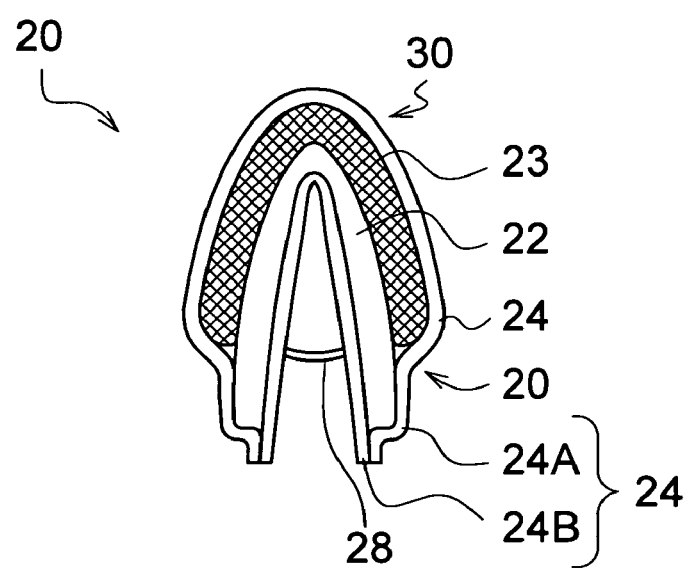
FIG. 4 is a cross sectional view illustrating the interlabial pad according to the first embodiment of the invention.

FIG. 4 is a cross sectional view illustrating the B-B' cross section of the pad 20 shown in FIG. 1, i.e., a cross section of the highly absorbing and retaining region 30. This highly absorbing and retaining region 30 comprises an absorbent body 22 and a second absorbent body 23 overlaid on the absorbent body 22. Dimension of the second absorbent body 23 is not particularly limited, but it is preferred that the dimension in the longitudinal direction be 5 to 180 mm, and particularly 10 to 100 mm, while the dimension in the lateral direction be 5 to 100 mm, and particularly 10 to 80 mm, with a thickness of 0.2 to 10 mm, and particularly 1 to 5 mm. The second absorbent body 23 preferably has a cross-sectional shape of a sharp convexity such that it can be more easily approached into the pudendal slit. In the sharp cross-sectional shape, apparent height of the second absorbent body 23 is greater than the apparent dimension in the lateral direction. The apparent dimension herein refers to a dimension of minimal distance when both ends are connected with a straight line one another.

Further, it is preferred that the second absorbent body 23 is smaller than the back face sheet 24B of the sheet element 24, taking into account of the leakage of the menstrual blood from the sheet element 24. It is preferred that entire dimension of the second absorbent body 23 in the longitudinal direction is in the range of from 10 to 50, while that in the lateral direction is in the range of from 10 to 50 in this case. Additionally, the apparent height is in the range of from 3 to 30 mm, and preferably in the range of from 1 to 20 mm. Although two absorbent bodies are used in this embodiment, one absorbent body may be used with altered lamination pattern of the absorbent body, or alternatively, two or more elements may be overlaid. Moreover, plane shape of the second absorbent body 23 is not particularly limited, which may be square, triangle, ellipsoid, inverted triangle, drop-like shape or the like. Among them, drop-like shape or the like having less lateral dimension as it extends backwards is preferred because it is liable to accommodate the shape of the labia.

Absorbent Body

Next, specific constitutions of the absorbent body 23nd the second absorbent body 23 shown in FIG. 3 and FIG. 4 are illustrated.

The absorbent body 22 and the second absorbent body 23 are constituted from pulp, chemical pulp, rayon, acetate, natural cotton, a polymer absorbent body, a fibrous polymer absorbent body, synthetic fiber, which may be used alone or as a mixture, and may be preferably bulky, hardly loose shape, and cause less chemical stimulation. Specifically, included may be nonwoven fabric sheets having a basis weight per unit area of 50 to 500 $g/m^2$ and a dimension of 1 to 20 mm, produced by laminating rayon or rayon acetate selected from those having a fineness falling within the range of from 1.1 to 6.6 dtex, at a mixing proportion of 95 to 60%, followed by forming a sheet of the fiber by subjecting to embossing. In connection with the process for producing the absorbent body 22 and the second absorbent body 23, a sheet obtained by an air laid process, a melt blown process, a span lace process, a paper making process or the like may be subjected to needling or embossing by passing between rolls with dots or a lattice shape arranged thereon. Percentage embossed area is preferably in the range of from 0.3 to 60%.

Sheet Element

Next, specific constitution of the sheet element 24 is illustrated. The sheet element 24 includes the front face sheet 24A and the back face sheet 24B.

For the front face sheet 24A, a material which is liquid permeable, liquid-hydrophilic and nonirritating to the skin is used. Examples of such a material include materials in which a nonwoven fabric obtained by a process of the production such as point bond, air through or the like is used alone, or any complex material of the same. Among such materials, those having a constitution including at least cellulose based liquid-hydrophilic fiber as a main component is preferred, taking into account of affinity with the inner wall of the labia such that the wearer does not feel unpleasant sense due to a foreign substance resulting from displacement caused between the interlabial pad and the inner wall of the labia. Specifically, spun lace nonwoven fabrics are preferred which are obtained by adjusting the fiber including a mixture with the proportion of 5 to 30% natural cotton and 70 to 95% rayon or acetate to have a basis weight per unit area in the range of from 20 to 50 g/m², followed by intertangling of the fiber by hydroentanglement and drying, and adjusting the thickness to fall within the range of from 0.3 to 1.0 mm. The thread type for use herein may be selected from those having a fiber length in the range of from 25 to 51 mm in cases of natural cotton, and those having a fiber length of 15 to 60 mm in cases of rayon or acetate, and having a fineness falling within the range of from 1.1 to 6.6 dtex. In addition, a film having permeabilize pores, or a film laminated on a fiber layer to arrange permeabilize pores may be also utilized.

In the front face sheet 24A, the region that contacts the outlet of the body fluids (hereinafter, referred to as "body fluid outlet contacting region") has a high permeability of body fluids. In order to elevate the permeability, reduction of the density by increasing the distance between fibers, arranging permeabilize pores, and the like may be exemplified.

According to specific examples of the film with pores, it is preferred that the pore size in the body fluid outlet contacting region be 0.2 to 5 mm, pitch be 0.2 to 10 mm, percentage area of pores be in the range of from 10 to 50%; and pore size of the adjacent region be 0.05 to 3 mm, pitch be 0.2 to 10 mm, percentage area of pores be in the range of from 3 to 30%. In the process for the production, so called PWF in which a film is passed through a pattern drum, the pore opening conditions of which had been previously altered, and the pores are opened by suction; or a process further adding the pores by pin embossing to the vestibular bed contacting region formed by PFW under conditions to arrange uniform pore opening may be executed. Arrangement of the pores is not particularly limited, which may be of hound's-tooth, lattice, wave or the like. Additionally, the shape of the pore may be circular, elliptic, square or the like. Moreover, a valve may be formed on the periphery of the pore. In this case, in order to avoid possible occlusion of the pore with the valve even though external pressure is placed, height of the valves particularly of the pores present in the body fluid outlet contactting region is preferably lower than the height of the valve in other adjacent region.

The back face sheet 24B which may be used has liquid impermeability such that leakage of the menstrual blood retained in the absorbent body outside of the interlabial pad can be prevented. Additionally, through the use of a moisture permeable material, accumulation of moisture during application can be reduced, thereby enabling sense of discomfort during the application to be lowered. Examples of such a liquid impermeable material include polyethylene, polypropylene, polyethylene terephthalate, polyvinyl alcohol, polylactic acid, polybutyl succinate, or nonwoven fabrics, paper, and laminated materials thereof, having a thickness of 15 to 60 μm. Alternatively, a breathable film may be used which is obtained by drawing a composite sheet of a resin and an inorganic filler. Specifically, films prepared using a low density polyethylene (LDPE) resin as a main component to have 10 to 30% pores, which is adjusted to fall within the range of the pore size of from 0.1 to 0.6 mm and the basis weight per unit area of 15 to 35 g/m² may be included. Examples of the nonwoven fabric include spun bond nonwoven fabrics, point bond nonwoven fabrics, through air nonwoven fabrics and the like, which may be subjected to a treatment to provide water repellency. Among them, SMS nonwoven fabrics including melt blown constituted from extra fine fibers with extremely small intrafiber distances are preferred. In this instance, it is preferably constituted to give the basis weight per unit area falling within the range of from 5 to 15 g/m², from 1 to 10 g/m², from 5 to 10 g/m².

Moreover, a mini sheet 28 may be affixed to the back face sheet 24B to permit easy application through inserting the wearer's finger between the mini sheet 28 and the back face sheet 24B upon application.

Mini Sheet

For the mini sheet 28, any material that is similar to those for the front face sheet 24A and the back face sheet 24B as described above can be used, however, a material having extendability or streatchability in the lateral direction is preferred. Use of such a material in the mini sheet 28 results in extension of the mini sheet 28 in the lateral direction depending on the width of the wearer's finger. Examples of the material having extendability or streatchability are illustrated below, but not limited thereto.

Examples of the material having streatchability include synthetic rubbers such as styrene-butadiene-styrene block copolymers (SBS), styrene-isoprene-styrene block copolymers (SIS) and urethane, films including an amorphous olefin based resin as a raw material, foam films with pores and the like. In addition, examples of the nonwoven fabric include spun lace nonwoven fabrics produced using a complex synthetic fiber having thermal shrinking properties, which is constituted from a core component having a high melting point and a sheath component having a low melting point, such as polyethylene (PE)/polypropylene (PP), PE/polyethylene terephthalate (PET) or PP/PP, as a raw material, followed by hydroentanglement; nonwoven fabrics of a shrink type in which thermal shrinkage is facilitated; and the like. Also, other available process for imparting extendability may be to arrange a broken cutting line or to cut out a circle.

The absorbent body 22, second absorbent body 23 and the sheet element 24, mini sheet 28 may be adhered using an agglutinant.

Agglutinant

Examples of the agglutinant include a variety of adhesives such as water base polymers, crosslinking agents, plasticizers, gel agglutinants including moisture, however, pressure-sensitive hot melt agglutinant is more preferably used taking into account of the stability of the application. Examples of the pressure-sensitive hot melt agglutinant exhibiting favorable stability of the application include mixtures prepared by melting 15 to 25% by weight of a styrene-ethylene butadiene-styrene block copolymer (SEBS), 15 to 35% by weight of a plasticizer, and 40 to 70% by weight of a agglutinating property-imparting agent. To this pressure-sensitive hot melt agglutinant may be added an antioxidant, a fluorescence protecting agent or the like in the range of from 0.1 to 1.0% by weight.

Second Embodiment

The interlabial pad 20A according to this embodiment has double sheet elements in the highly absorbing and retaining region 30A.

The highly absorbing and retaining region 30A includes a first sheet element 26A and a second sheet element 27A each having a body fluid absorption capacity. The first sheet element 26A has an absorbent body 22A and is preferably constituted from the similar material to that for use in the sheet element 24 of the first embodiment. The second sheet element 27A may include a layered product of an absorbent body that absorbs and retains the body fluids, and a sheet for packaging the same in some cases, or may consist of only a liquid permeable material that can remove the body fluids from the body and then readily permeabilize them to the first sheet element 26A in other cases. The sheet for packaging the absorbent body in the former case may consist of only a liquid permeable material, or a sheet having a back face made from a liquid impermeable material. In the latter case, compliance and adhesiveness to the labia are remarkably enhanced because the second sheet element has extremely favorable flexibility.

Figure 5:
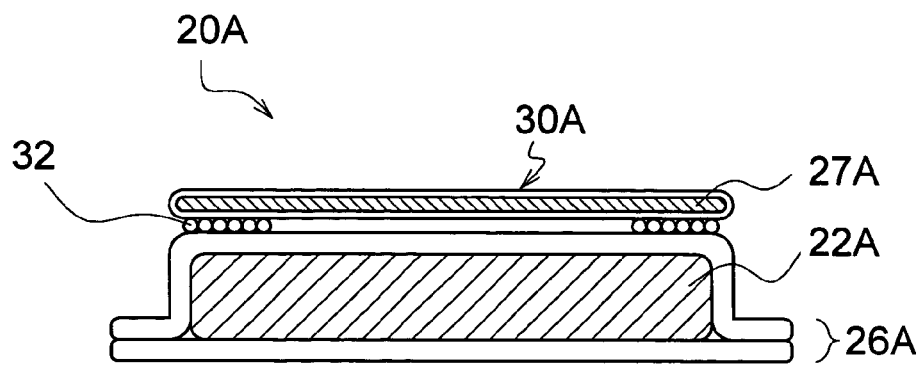
FIG. 5 is a cross sectional view illustrating an interlabial pad according to a second embodiment of the invention.

FIG. 5 shows a cross section of the highly absorbing and retaining region 30A of the pad 20A according to this embodiment. The second sheet element 27A is disposed on a face of the first sheet element 26A to be brought into contact with the body. Dimension of the second sheet element 27A in the lateral direction may be the same as the dimension of the first sheet element 26A in the lateral direction, however, the dimension of the second sheet element 27A is preferably smaller than that of the back face sheet of the first sheet element 26A in light of the leakage of menstrual blood from the first sheet element 26A. The second sheet element 27A may be just fixed at a part thereof to contact the first sheet element 26A, for example side edge portion 32 may be fixed to the first sheet element 26A. Accordingly, the second sheet element 27A can readily comply with the movement of the wearer's labia.

Figure 6:
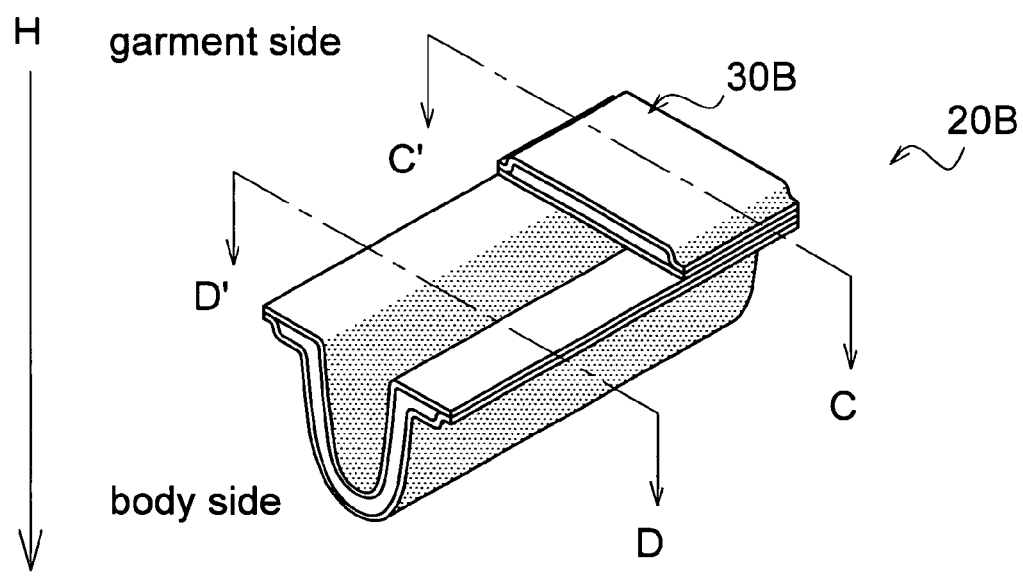
FIG. 6A is a front perspective view illustrating an interlabial pad according to a modified embodiment of the second embodiment of the invention.
FIG. 6B is a cross sectional views illustrating the interlabial pad according to the modified embodiment.
FIG. 6C is a cross sectional views illustrating the interlabial pad according to the modified embodiment.
Figure 6:
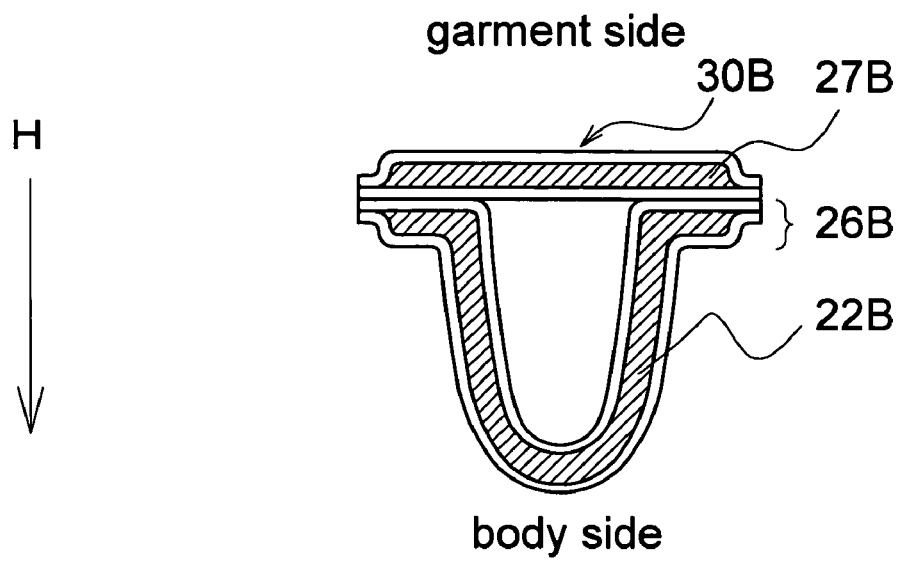
Figure 6:
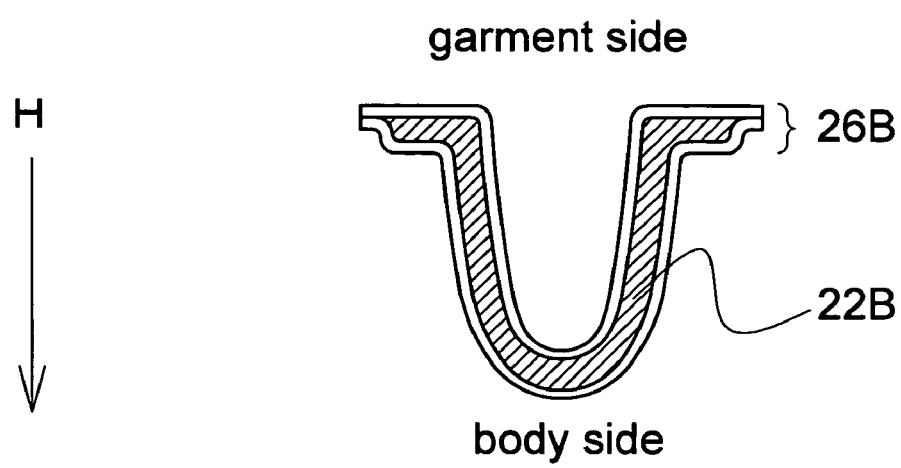

Moreover, in a modified example of this embodiment, arrangement of the first sheet element 26A and the second sheet element 27A may be inverted. In FIGS. 6A to 6C, an interlabial pad 20B as a modified example of the second embodiment is shown. In these figures, the view is depicted upside down from the state of application in order to encourage accurate comprehension of the arrangement of the first sheet element 26B and the second sheet element 27B. As is shown in FIG. 6A, when the second sheet element 27B is disposed beneath the first sheet element 26B, a part of the first sheet element 26B to which the second sheet element 27B is positioned preferably has liquid permeability that allows permeabilization of the absorbed body fluids toward the second sheet element 27B, as specifically described in connection with the front face sheet 24A and the back face sheet 24B according to the first embodiment. In this figure, vertical direction (H-axis direction) corresponds to the body-facing side to be brought into contact with the wearer's body.

To the contrary, the other part of the first sheet element 26B to which the second sheet element 27B is not positioned preferably has a back face sheet which is liquid impermeable to avoid substantial leakage of the absorbed body fluids downwards, as specifically shown in FIG. 1 according to the first embodiment. Additionally, as another example may be included a first sheet element which has a back face sheet of a spun lace nonfibrous fabric adjusted to have a thickness falling within the range of from 0.3 to 1.0 mm to cover the entire face of the back face of the absorbent body, while lamination is executed in the region to which the second sheet element 27B is not positioned.

Cross section of the high absorption capacity region 30B of the pad 20B (C-C' cross section) includes the first sheet element 26B and the second sheet element 27B as shown in FIG. 6B. The first sheet element 26B includes the absorbent body 22B that absorbs and retains the body fluids, and a sheet for packaging the same. The sheet for packaging the absorbent body may consist of only a liquid permeable material, or a sheet having the back face made from a liquid impermeable material. However, the first sheet element 26B with which the second sheet element 27B is disposed preferably has liquid permeability that allows permeabilization of the absorbed body fluids toward the second sheet element 27B. Further, as shown in FIG. 6C, a part of the first sheet element 26B to which the second sheet element 27B is not positioned (D-D' cross section) preferably has a back face sheet which is liquid impermeable to avoid substantial leakage of the absorbed body fluids downwards.

Third Embodiment

The interlabial pad 20C according to this embodiment has a gap formed between a second sheet element 27C and a first sheet element 26C.

Figure 7:
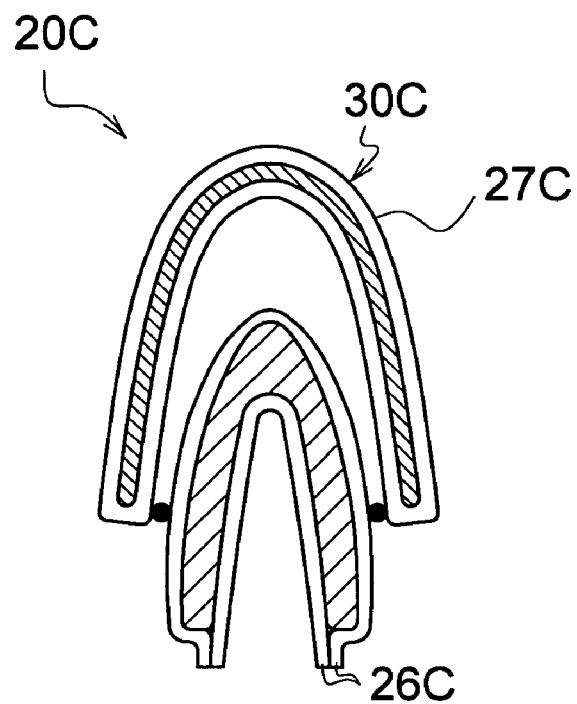
FIG. 7 is a cross sectional view illustrating the interlabial pad according to a third embodiment of the invention.

FIG. 7 shows a cross section of the highly absorbing and retaining region 30C of the pad 20C according to the third embodiment which was folded in two. Although the second sheet element 27C is disposed on the first sheet element 26C, dimension of the second sheet element 27C in the lateral direction is set to be longer than that of the second embodiment. Therefore, a gap is formed with the first sheet element 26C in between. The wearer can also apply the pad 20C through inserting her finger into the gap. In this case, it is preferred that the second sheet element 27C is made from a material having streatchability, or a cut line or the like is arranged to enable to gain streatchability.

Fourth Embodiment

The interlabial pad 20D according to this embodiment has a slit 34 arranged in the highly absorbing and retaining region 30D.

Figure 8:
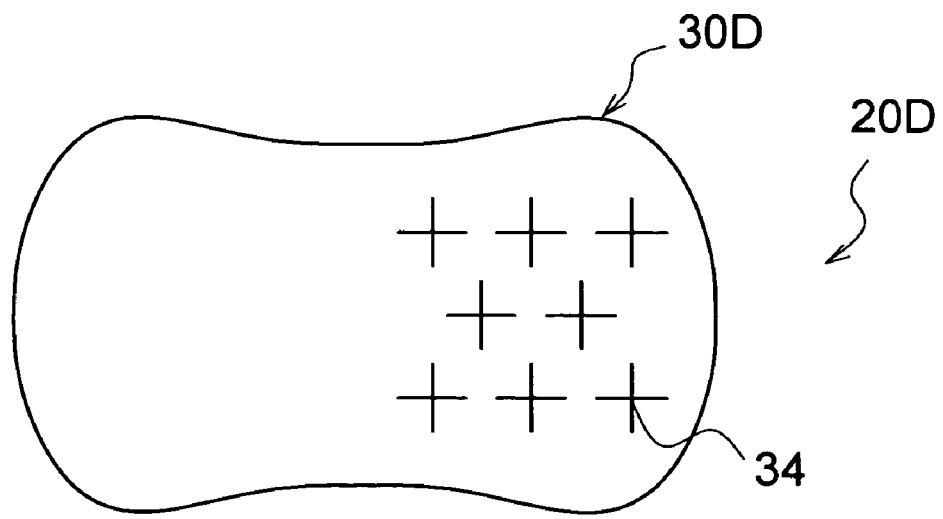
FIG. 8 is a plane view illustrating the interlabial pad according to the fourth embodiment of the invention.

FIG. 8 is a plane view illustrating the pad 20D according to this embodiment. Slits 34 are arranged on the highly absorbing and retaining region 30D. Thus, diffusion by way of the capillary phenomenon of the body fluids reached to the slit 34 is prevented. Further, although the shape of this slit 34 is not particularly limited, flexibility can be imparted to the pad 20D by making the slits in both longitudinal direction and lateral direction. Compliance and adhesiveness to the labia are thereby enhanced. This slit 34 may be arranged also on the highly absorbing and retaining region of the pad according to the embodiments 1 to 3.

Fifth Embodiment

Materials of constituent members of the interlabial pad according to this embodiment have biodegradability, water dispersibility and water solubility.

It is preferred that the interlabial pad of the invention is constituted from a biodegradable material and/or a water dispersible material and/or water soluble material. Such an interlabial pad can be flushed by dropping into the toilet after use just as it is. Employed shape of the pad according to this embodiment is similar to that of the pad 20 of the first embodiment and the figure showing the pad is omitted.

For reference, "biodegradability" refers to possible decomposition in the presence of a microorganism, in accordance with a process in nature. "Water dispersibility" has the same meaning as degradability in water, referring to the property of fibers being readily dispersed into small pieces in a large quantity of water or a stream of water. "Water solubility" refers to a property of dissolution in a large quantity of water or a stream of water although not affected by a limited amount of moisture upon use (particularly, menstrual blood).

Front Face Sheet

Examples of the material which may be used in the front face sheet include wet spun lace nonwoven fabrics with the fiber length selected from the range of from 1 to 15 mm, in addition to the spun lace nonwoven fabrics. Other materials which may be used include biodegradable resins obtained by hydrolysis of polylactic acid, polybutylene succinate and the like. For example, melt blown nonwoven fabrics which are produced using polylactic acid as a raw material and which are adjusted to give the specific weight per unit area falling within the range of from 20 to 60 g/m², as well as spun bond nonwoven fabrics adjusted to give the specific weight per unit area falling within the range of from 15 to 30 g/m² and a fineness falling within the range of from 1.1 to 3.3 dtex. Each nonwoven fabric material may be or may not be subjected to a treatment for opening pores.

Absorbent Body and Second Absorbent Body

Examples of the material which may be used in the absorbent body and the like include nonwoven fabric sheets obtained by needling. In light of the biodegradability of the polymer absorbent material, use of a carboxymethylcellulose finer is preferred.

Back Face Sheet

Examples of the material which may be used in the back face sheet include: polyvinyl alcohol (PVA) films; film sheets produced by subjecting one face or both faces, or a part of a PVA film to a treatment to provide water repellency with silicone or the like; starch films; films which are produced using a biodegradable resin as a raw material prepared by hydrolysis of polylactic acid, polybutylene succinate or the like; and laminated paper such as tissues. The sheet may be colored by admixing with an inorganic pigment in the range of 0.1 to 5% as needed.

Mini Sheet

Examples of the material which may be used in the mini sheet include: films which are produced using a biodegradable material such as polylactic acid or polybutylene succinate as a raw material; spun bond nonwoven fabrics, melt blown nonwoven fabrics and the like; or films, nonwoven fabrics and the like produced using a water soluble material such as PVA or CMC as a raw material; and water dispersible tissues, spun lace nonwoven fabrics and the like that are produced using a cellulose fiber, a regenerated cellulose fiber or the like as a main component.

Specifically, mini sheets obtained by subjecting a sheet which is a spun bond nonwoven fabric or a melt blown nonwoven fabric including a biodegradable material as a main component, and which is adjusted to give the fineness falling within the range of from 0.1 to 3.3 dtex and the specific weight per unit area falling within the range of from 15 to 40 g/m², to a corrugate processing are preferred.

The present invention can be utilized as an interlabial pad characterized by avoiding extensive exudation of body fluids by improving a body fluid absorption capacity and a body fluid retaining capacity in a portion of the interlabial pad which contacts the site where body fluids are discharged.

What is claimed is:

1. An interlabial pad adapted for absorbing body fluid with at least a part of the pad between the labia of a wearer, comprising:
    a liquid permeable front face sheet;
    a liquid impermeable back sheet;
    an elongated planar first absorbing body enclosed between the front face sheet and the back sheet;
    a planar second absorbent body provided on one side of the first absorbent body in a longitudinal direction thereof;
    a body fluid outlet contacting region provided with the second absorbent body to contact at least one of an ostium vaginae and an urethral meatus; and
    a plurality of slits provided on the body fluid outlet contacting region, formed pair-wise in a cross-shape, the cross-shaped slits being aligned in at least three longitudinal lines,
    wherein the interlabial pad is configured to be folded in two when worn,
    wherein slits in a middle line of the at least three longitudinal lines substantially define a center line of the interlabial pad when the interlabial pad is folded in two, and
    wherein the interlabial pad is made of at least one of a material selected from the group consisting of biodegradable materials, water-dispersible materials and water-soluble materials.

2. The interlabial pad according to claim 1, wherein the second absorbent body has a length of 10 mm to 100 mm in the longitudinal direction, and a length of 10 mm to 80 mm in a lateral direction.

3. The interlabial pad according to claim 1, wherein a diameter of the pore in the body fluid outlet contacting region is 0.20 mm to 5 mm, and the diameter of the pore in the other than the body fluid outlet contacting region is 0.05 mm to 3 mm.

4. An interlabial pad adapted for absorbing body fluid with at least a part of the pad between The labia of a wearer, comprising:
    a first sheet element and a second sheet element,
    the first sheet element comprising:
        a liquid permeable front face sheet,
        a liquid impermeable back sheet; and
        an elongated planar first absorbent body enclosed between the front face sheet and the back sheet;
    the second sheet element comprising:
        a liquid permeable front face sheet,
        a liquid impermeable back sheet;
        a planar second absorbent body enclosed between the front face sheet and the back sheet;
        side edges in a longitudinal direction of the first sheet element; and
        a body fluid outlet contacting region provided with the second absorbent,
    wherein the second sheet element is provided on the first sheet element in a longitudinal direction thereof to contact at least one of an ostium vaginae and a urethral meatus, and
    wherein a width of the second sheet element is longer than a width of the first sheet element, whereby the second sheet element forms a bight-shaped gap between the first sheet element and the second sheet element when the side edges of the second sheet element are bonded to the first sheet element.

5. The interlabial pad according to claim 4, wherein the front face sheet of the second sheet element is liquid permeable, and the back sheet of the second sheet element is liquid permeable.

6. The interlabial pad according to claim 4, wherein the interlabial pad is made of at least one of a material selected from the group consisting of biodegradable materials, water-dispersible materials and water-soluble materials.

7. An interlabial pad adapted for absorbing body fluid with at least a part of the pad between the labia of a wearer, comprising;
    a first sheet element with planar shape and a second sheet element with planar shape;

the first sheet element comprising:
- a liquid permeable front face sheet,
- a liquid impermeable back sheet, and
- an elongated planar first absorbent body enclosed between the front face sheet and the back sheet;

the second sheet element comprising;
- a liquid permeable front face sheet,
- a liquid semi-permeable back sheet,
- a planar second absorbent body enclosed between the front face sheet and the back sheet,
- a side edge in the longitudinal direction of the first sheet element, and
- a body fluid outlet contacting region provided with the second absorbent body;

wherein the second sheet element is provided on the first sheet element in a longitudinal direction thereof to contact at least one of an ostium vaginae and a urethral meatus, and wherein a width of the second sheet element is longer than a width of the first sheet element, whereby the second sheet element forms a bight-shaped gap between the first sheet element and the second sheet element when the side edges of the second sheet element are bonded to the first sheet element.

* * * * *